(12) United States Patent
Holler et al.

(10) Patent No.: US 6,303,334 B1
(45) Date of Patent: *Oct. 16, 2001

(54) NUCLEIC ACID ENCODING A TRANSDOMINANT NEGATIVE RETROVIRAL INTEGRASE

(75) Inventors: Tod Paul Holler, Ann Arbor; Annette Meyer, Brighton; Gary Jan Nabel; Leonard Post, both of Ann Arbor, all of MI (US)

(73) Assignees: Warner Lambert Company; University of Michigan, both of Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/231,182

(22) Filed: Jan. 14, 1999

Related U.S. Application Data

(62) Division of application No. 08/841,179, filed on Apr. 29, 1997, now Pat. No. 5,908,923, which is a division of application No. 08/286,578, filed on Aug. 5, 1994, now abandoned.

(51) Int. Cl.[7] .......................... C12N 15/11; C12N 15/85; C07H 21/02; A61K 48/00; A61K 35/00
(52) U.S. Cl. ..................... 435/69.1; 435/325; 435/320.1; 435/455; 514/44; 424/93.1; 424/93.21; 536/23.1
(58) Field of Search ......................... 424/93.21; 536/23.1; 435/320.1; 514/44

(56) References Cited

U.S. PATENT DOCUMENTS

| | | |
|---|---|---|
| 5,217,889 | 6/1993 | Roninson et al. . |
| 5,512,421 * | 4/1996 | Burns et al. ................. 435/320.1 |
| 5,616,459 * | 4/1997 | Kramer et al. ................ 435/5 |
| 5,908,923 * | 6/1999 | Holler et al. .............. 536/23.1 |
| 5,993,972 * | 1/1997 | Weiner et al. ................ 514/44 |
| 6,001,810 * | 12/1999 | Hui et al. ..................... 514/17 |

FOREIGN PATENT DOCUMENTS

WO 92/03578   3/1992   (WO) .

OTHER PUBLICATIONS

Ngo et al., The protein folding problem and tertiary structure prediction, Merz et al., ed., Birkhauser, Boston, MA, pp. 433 and 492–495, 1994.*
Dropulic et al., Human Gene Therapy, vol. 5, pp. 927–939, 1994.*
Holler et al. Gene, vol. 136, pp. 323–328, 1993.*
"Methods In Electroporation: Gene Pulser Electro Proctocols", Bio–Rad Laboratories,Inc., (1993).
Bahner, et al., "Comparison of Trans–Dominant Inhibitor", *Journal of Virology*, vol. 67, pp. 3199–3207 (1993).
Baltimore, D., *Nature*, vol. 335, pp. 395–396 (1988).
Bevec et al., *Proc. Natl. Acad. Sci. USA*, vol. 89, pp. 9870–9874 (1992).
Cochran et al., *Journal of Virology*, vol. 65, pp. 5305–5313 (1991).
Dropulic et al., "Gene Therapy For HIV Infection", *Human Gene Therapy*, vol. 5, pp. 927–939 (1994).
Feinberg et al., *AIDS Research and Human Retroviruses*, vol. 8, No. 6, pp. 1013–1022 (1992).
Holler, T. et al., *Gene* , vol. 136, pp. 323–328 (1993).
LaFemina, R. et al., *Journal of Virology*, vol. 66, pp. 7414–7419 (1992).
Malim, M. et al., *Cell*, vol. 58, pp. 205–214 (1989).
Mumm, S. et al. *Virology*, vol. 189, pp. 500–510 (1992).
Petrovskis, E. et al., *Journal of Virology*, vol. 62, pp. 2196–2199 (1988).
Robinson, H. et al., *Journal of Virology*, vol. 40, pp. 745–751 (1981).
Rodner et al., *Archives of Virology*, vol. 131, No. 1–2, pp. 177–183 (1993).
Sakai, H. et al., *Journal of Virology*, vol. 67, pp. 1169–1174 (1993).
Sanford, J. et al., *J. Theor. Biol.*, vol. 113, pp. 395–405 (1985).
Sullenger, B. et al., *Cell*, vol. 63, pp. 601–608 (1990).
Trono et al., *Cell*, vol. 59, No. 1, pp. 113–120 (1989).
Walker, J. et al., *The Language of Biotechnology a Dictionary of Terms*, Second Edition, American Chemical Society, Washington, D.C., page v and pp. 274–275 (1995).
Wilson, T., *Proc. Natl. Acad. Sci. USA*, vol. 90, pp. 3134–3141 (1993).
Yu, M. et al., *Gene Therapy*, vol. 1, pp. 13–26 (1994).

* cited by examiner

*Primary Examiner*—Deborah J. R. Clark
*Assistant Examiner*—Michael C. Wilson
(74) *Attorney, Agent, or Firm*—Merchant & Gould, P.C.

(57) ABSTRACT

A method of using a transdominant negative integrase gene to make at least one cell resistant to a retroviral infection which includes retroviral infections resulting from HIV; a method for introducing a transdominant negative integrase gene into at least one mammalian cell to make said cell resistant to a retroviral infection as well as vectors, cells, and methods of constructing same useful in the afore-mentioned methods; a method of treating AIDS comprising administering to a patient an effective amount of a transdominant negative integrase gene alone or combined with agents useful for gene therapy inhibition of HIV, antiviral agents, or interleukin-2; and pharmaceutical delivery methods which include a transdominant negative integrase gene alone or combined with agents useful for gene therapy inhibition of HIV, antiviral agents, or interleukin-2.

22 Claims, 1 Drawing Sheet

FIG. 1

SEQUENCE LISTING

```
<160> NUMBER OF SEQ ID NOS: 4

<210> SEQ ID NO 1
<211> LENGTH: 900
<212> TYPE: DNA
<213> ORGANISM: Artificial Sequence
<220> FEATURE:
<223> OTHER INFORMATION: Description of Artificial Sequence:  Encoding
      HIV Integrase

<400> SEQUENCE: 1
ccaagcttgg gccaccatgg ccttcctgga cggtatcgat aaagctcagg aagaacacga      60
aaaataccac tctaactggc gcgccatggc ttctgacttc aacctgccgc cggttgttgc     120
caaggaaatc gtggcttctt gcgacaaatg ccaattgaaa ggtgaagcta tgcatggtca     180
ggtcgactgc tctccaggta tctggcagct ggactgcact catctcgagg gtaaagttat     240
cctggttgct gttcacgtgg cttccggata catcgaagct gaagttatcc cggctgaaac     300
cggtcaggaa actgcttact tcctgcttaa gctggccggc cgttggccgg ttaaaactgt     360
tcacactgac aacggttcta acttcactag tactactgtt aaagctgcat gctggtgggc     420
cggcatcaaa caggagttcg ggatcccgta caacccgcag tctcagggcg ttatcgaatc     480
tatgaacaaa gagctcaaaa aaatcattgg ccaggtacgt gatcaggctg agcacctgaa     540
aaccgcggtg cagatggctg ttttcatcca caacttcaaa cgtaaaggtg gtatcggtgg     600
ttacagcgct ggtgaacgta tcgttgacat catcgctact gatatccaga ctaaagaact     660
gcagaaacag atcactaaaa tccagaactt ccgtgtatac taccgtgact ctagagaccc     720
```

```
ggtttggaaa ggtcctgcta aactcctgtg gaagggtgaa ggtgctgttg ttatccagga      780
caactctgac atcaaagtgg taccgcgtcg taaagctaaa atcattcgcg actacggcaa      840
acagatggct ggtgacgact gcgttgctag ccgtcaggac gaagactaaa agcttcaggc      900
```

<210> SEQ ID NO 2
<211> LENGTH: 290
<212> TYPE: PRT
<213> ORGANISM: Artificial Sequence
<220> FEATURE:
<223> OTHER INFORMATION: Description of Artificial Sequence: HIV Integrase

<400> SEQUENCE: 2

```
Met Ala Phe Leu Asp Gly Ile Asp Lys Ala Gln Glu Glu His Glu Lys
 1               5                   10                  15

Tyr His Ser Asn Trp Arg Ala Met Ala Ser Asp Phe Asn Leu Pro Pro
            20                  25                  30

Val Val Ala Lys Glu Ile Val Ala Ser Cys Asp Lys Cys Gln Leu Lys
        35                  40                  45

Gly Glu Ala Met His Gly Gln Val Asp Cys Ser Pro Gly Ile Trp Gln
    50                  55                  60

Leu Asp Cys Thr His Leu Glu Gly Lys Val Ile Leu Val Ala Val His
65                  70                  75                  80

Val Ala Ser Gly Tyr Ile Glu Ala Glu Val Ile Pro Ala Glu Thr Gly
                85                  90                  95

Gln Glu Thr Ala Tyr Phe Leu Leu Lys Leu Ala Gly Arg Trp Pro Val
            100                 105                 110

Lys Thr Val His Thr Asp Asn Gly Ser Asn Phe Thr Ser Thr Thr Val
        115                 120                 125

Lys Ala Ala Cys Trp Trp Ala Gly Ile Lys Gln Glu Phe Gly Ile Pro
    130                 135                 140

Tyr Asn Pro Gln Ser Gln Gly Val Ile Glu Ser Met Asn Lys Glu Leu
145                 150                 155                 160

Lys Lys Ile Ile Gly Gln Val Arg Asp Gln Ala Glu His Leu Lys Thr
                165                 170                 175

Ala Val Gln Met Ala Val Phe Ile His Asn Phe Lys Arg Lys Gly Gly
            180                 185                 190

Ile Gly Gly Tyr Ser Ala Gly Glu Arg Ile Val Asp Ile Ile Ala Thr
        195                 200                 205

Asp Ile Gln Thr Lys Glu Leu Gln Lys Gln Ile Thr Lys Ile Gln Asn
    210                 215                 220

Phe Arg Val Tyr Tyr Arg Asp Ser Arg Asp Pro Val Trp Lys Gly Pro
225                 230                 235                 240

Ala Lys Leu Leu Trp Lys Gly Glu Gly Ala Val Val Ile Gln Asp Asn
                245                 250                 255

Ser Asp Ile Lys Val Val Pro Arg Arg Lys Ala Lys Ile Ile Arg Asp
            260                 265                 270

Tyr Gly Lys Gln Met Ala Gly Asp Asp Cys Val Ala Ser Arg Gln Asp
        275                 280                 285

Glu Asp
    290
```

<210> SEQ ID NO 3
<211> LENGTH: 35
<212> TYPE: DNA

-continued

```
<213> ORGANISM: Artificial Sequence
<220> FEATURE:
<223> OTHER INFORMATION: Description of Artificial Sequence:  Synthetic
      Oligonucleotides

<400> SEQUENCE: 3
ccaagctggg ccaccatggc cttcctggac ggtat                              35

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence:  Synthetic
      Oligonucleotides

<400> SEQUENCE: 4
cgataccgtc caggaaggcc atggtggccc aagcttgg                           38
```

NUCLEIC ACID ENCODING A TRANSDOMINANT NEGATIVE RETROVIRAL INTEGRASE

This application is a divisional of application Ser. No. 08/841,179, filed Apr. 29, 1997, U.S. Pat. No. 5,908,923, which is a divisional of application Ser. No. 08/286,578, filed Aug. 5, 1994, now abandoned.

BACKGROUND OF THE INVENTION

The present invention relates to a medical method of treatment. In particular, the present invention concerns the use of a transdominant negative integrase gene to make at least one mammalian cell resistant to a retroviral infection, to methods for their production, to pharmaceutical delivery methods which include these genes, and to pharmaceutical methods of treatment. More particularly, the novel transdominant negative integrase gene alone or combined with another gene that confers protection from human immunodeficiency virus (HIV) such as, for example, a transdominant negative rev gene and/or a ribozyme that cleaves HIV ribonucleic acid (RNA) is useful in treating acquired immunedeficiency syndrome (AIDS).

AIDS results from HIV infection which depletes $CD4^+T$ cells. Currently, there is no effective treatment for AIDS. One of the most attractive and least exploited targets for the therapy of AIDS is the viral integrase (Brown P. O., "Integration of Retroviral DNA". In: *Current Topics in Microbiology of Immunology,* 157:19–48 (1990)). The life cycle of retroviruses is dependent on integration into the host chromosome. For HIV, integration is necessary for viral replication (LaFemina R. L., et al., *Journal of Virology,* 66:7414–7419 (1992) and Sakai H., et al., *Journal of Virology,* 67:1169–1174 (1993)). This process is mediated by integrase, a viral protein. One approach to inhibition of the essential integration process is to express some form of integrase that will block the integrase function of the incoming HIV. This is based on the concept of "pathogen-derived resistance" disclosed by Sanford J. C. and Johnston S. A., *J. Theor. Biol.,* 113:395–405 (1985). Pathogen-derived resistance is based on the strategy that expression of certain genes from pathogens inhibit replication of such pathogens. Various examples of this concept have been disclosed including: retroviral envelope genes (Robinson H. L., et al., *Journal of Virology,* 40:745–751 (1981)); coat protein genes of plant viruses (Wilson T. M. A., *Proc. Natl. Acad. Sci. USA,* 90:3134–3141 (1993)); envelope glycoprotein genes of herpes viruses (Petrovskis E. A., et al., *Journal of Virology,* 62:2196–2199 (1988)); transdominant negative HIV rev (Malim M. H., et al., *Cell,* 58:205–214 (1989)); over-expression of HIV tar sequences as "decoys" (Sullenger B. A., et al., *Cell,* 63:601–608 (1990)); and transdominant negative mutants of HIV gag. In the case of HIV, this concept of pathogen-derived resistance was later termed "intracellular immunization" (Baltimore D., *Nature,* 335:395–396 (1988)).

However, prior to the present invention, there was no suggestion that retroviral integrase could be made to exert a transdominant negative phenotype. In fact, since integrase enters a cell with the virion and is presumed to remain part of the preintegration complex, it was regarded by many as an unlikely candidate for being amenable to interference by a transdominant negative mutant. In a recent review on gene therapy of AIDS (Yu M., et al., *Gene Therapy,* 1:13–26 (1994)), many possibilities were discussed with no mention of integrase as a target. Additionally, prior to the present invention, there was no good technology for exploring the possibility of a transdominant negative integrase. Retroviral integrases are made as part of polyprotein precursors (the "gag-pol precursor") in infected cells. There is no natural expression of a retroviral integrase in a mammalian cell without many other viral proteins that are part of the precursor. Although there is a report of expression of Rous sarcoma virus integrase alone (Mumm S. R., et al., *Virology,* 189:500–510 (1992)), expression of HIV integrase has been problematic. This problem has been attributed to a rev-responsive element within the integrase gene (Cochrane, et al., *J. Virol.,* 65:5305–5313 (1991)). Holler T. P., et al., *Gene,* 136:323–328 (1993) reported the synthesis of genes coding for wild-type ("NdeI") and an inactive mutant ("D116N:) integrase for expression in *E. coli.*

Thus, an object of the present invention is the expression of HIV integrase in mammalian cells. Efficient expression of HIV integrase was achieved in the present invention by employing a synthetic gene for expression in mammalian cells (Seq ID No.: 1). That this was successful was an unpredictable and surprising result, since the synthetic gene used was synthesized to optimize codon usage for the bacterium *E. coli.* Bacterial genes could have sequences recognized by mammalian cells as splice sites or methylation sites for inactivation of the gene, making the successful expression of a bacterial gene in mammalian cells highly unpredictable.

SUMMARY OF THE INVENTION

Accordingly, the present invention is directed to a method of using a transdominant negative integrase gene to make at least one cell resistant to a retroviral infection.

In a preferred embodiment of the first aspect of the invention, the retroviral infection is selected from the group consisting of: HIV; HTLV I; HTLV II; equine infections anemia virus; bovine leukemia virus; murine retrovirus; and avian leukosis virus, and the cell is selected from the group consisting of a mammalian cell and an avian cell.

In a most preferred embodiment of the first aspect of the invention, the retroviral infection is HIV and the cell is a human cell.

In a second aspect, the present invention is directed to a method for introducing a transdominant negative integrase gene into at least one mammalian cell to make said cell resistant to a retroviral infection, comprising introducing the DNA into at least one mammalian cell by a process of delivery selected from the group consisting of:
  a) use of calcium phosphate co-precipitation;
  b) in a complex of cationic liposomes:
  c) electroporation;
  d) receptor mediated endocytosis;
  e) naked DNA;
  f) transduction by a viral vector; and
  g) particle-mediated gene transfer (Cheng L., et al., *Proc. Natl. Acad. Sci. USA,* 90:4455–4459 (1993) and Yang N-S., *Critical Reviews in Biotechnology,* 12:335–356 (1992)).

In a preferred embodiment of the second aspect of the invention, the transdominant negative integrase gene is HIV integrase and the mammalian cell is a human cell.

In a most preferred embodiment of the second aspect of the invention, the human cell is selected from the group consisting of a $CD4^+T$ lymphocyte, a monocyte, and a hematopoietic progenitor cell, and the viral vector is selected from the group consisting of: retrovirus; adenovirus; adeno-associated virus; and herpes virus.

In a third aspect, the present invention is directed to a method for introducing a transdominant negative integrase gene into at least one mammalian cell to make said cell resistant to a retroviral infection comprising inserting said transdominant negative integrase gene into a vector and expressing transdominant negative integrase in said at least one mammalian cell.

In a preferred embodiment of the third aspect of the invention, the transdominant negative integrase gene is HIV integrase; the vector is selected from the group consisting of: pRSV/IN-NdeI and pRSV/IN-D116N; and the mammalian cell is 293-CD4.

In a more preferred embodiment of the third aspect of the invention, the transdominant negative integrase gene is HIV integrase; the vector is pRSV/IN-NdeI; and the mammalian cell is 293-CD4.

In a most preferred embodiment of the third aspect of the invention, the transdominant negative integrase gene is HIV integrase; the vector is pRSV/IN-NdeI; and the mammalian cell is a human cell selected from the group consisting of a CD4$^+$T lymphocyte, a monocyte, and a hematopoietic progenitor cell.

In a fourth aspect, the present invention is directed to a method of constructing the pRSV/IN-NdeI vector comprising inserting the HIV integrase gene into the pRcRSV vector to afford the pRSV/IN-NdeI vector.

In a fifth aspect, the present invention is directed to a vector for production of HIV transdominant negative integrase comprising a DNA sequence encoding HIV integrase.

In a preferred embodiment of the fifth aspect of the invention, the vector is selected from the group consisting of pRSV/IN-NdeI and pRSV/IN-D116N.

In another preferred embodiment of the fifth aspect of the invention, the vector is pRSV/IN-NdeI.

In a more preferred embodiment of the fifth aspect of the invention, the DNA sequence contains a substantial number of codons different from the natural codons, preferably 10 or more codons different from the natural codons.

In a most preferred embodiment of the fifth aspect of the invention, the DNA sequence is Seq ID No.: 1 or a DNA sequence containing 10 or less condons different from Seq ID No.: 1 or a fragment thereof that encodes at least 150 amino acids; and expression is carried out in a eukaryotic cell, preferably a mammalian cell.

In a sixth aspect, the present invention is directed to the synthetic gene of Seq ID No.: 1 or a synthetic gene having a DNA sequence containing 10 or less codons different from Seq. ID. No.: 1 or a fragment thereof that encodes at least 150 amino acids.

In a seventh aspect, the present invention is directed to a highly transfectable cell line which is transduced to express human CD4.

In a most preferred embodiment of the seventh aspect of the invention, the highly transfectable cell line is 293-CD4.

In an eighth aspect, the present invention is directed to a method of constructing a 293-CD4 cell comprising inserting the CD4 coding sequence into a vector and transfecting the vector into 293 cells.

In a most preferred embodiment of the eighth aspect of the invention, the vector is RSV-CD4.

In a ninth aspect, the present invention is directed to a method of preparing a retroviral integrase comprising inserting a synthetic integrase gene into a vector and expressing said vector in a mammalian cell.

In another preferred embodiment of the ninth aspect of the invention, the retroviral integrase is HIV integrase.

In a more preferred embodiment of the ninth aspect of the invention, the synthetic integrase gene contains a substantial number of codons different from the natural codons, preferably 10 or more codons different from the natural codons.

In a most preferred embodiment of the ninth aspect of the invention, the synthetic integrase gene is Seq ID No.: 1 or a DNA sequence containing 10 or less codons different from Seq ID No: 1 or fragment thereof that encodes at least 150 amino acids.

A transdominant negative integrase gene could be delivered (by a retrovirus or other gene delivery method) to CD4$^+$T cells from an HIV-infected patient ex vivo, then re-introduced into the patient. This would give the patient a population of T cells that would be resistant to infection by HIV. Additionally, a transdominant negative integrase gene could be delivered (by a retrovirus or other gene delivery method) to hematopoietic progenitor cells. Such cells can be derived from bone marrow or from peripheral blood after stimulation by a cytokine such as, for example, G-CSF. These transduced cells are then reintroduced into the patient. This would give a population of hematopoietic cells, including CD4$^+$T cells that would be resistant to HIV.

Use of a transdominant negative integrase gene as a method of treatment of AIDS is based on the following scientific rationale:

1. Integrase is an essential protein for HIV infection. Genetic analysis of HIV integrase mutations (LaFemina R. L., et al., *Journal of Virology*, 66:7414–7419 (1992) and Sakai H., et al., *Journal of Virology*, 67:1169–1174 (1993)) shows that integrase is essential for HIV infection to proceed. Additional genetic analysis by Shin, C-G., et al., *Journal of Virology*, 68:1633–1642 (1994) shows that changes in integrase can have pleiotropic effects on a variety of steps in the HIV life cycle. Although we do not yet know the step in the HIV life cycle where the dominant negative integrase is having its effect, it is clearly a vulnerable target for interfering with replication of virus.

2. Cell culture results where HIV replication is blocked is the accepted criterion by the AIDS research community and regulatory authorities for clinical testing. This includes cell culture effect of transdominant negative mutants of retroviral proteins, as exemplified by the approval of clinical testing of rev M10 (Nabel G., et al., *Human Gene Therapy*, 5:79–92 (1994)).

3. Transdominant negative genes active in cell culture provide pathogen-derived resistance at the level of an intact multicellular organism. Examples include retroviral envelope genes and plant virus coat protein genes (Robinson H. L., et al., *Journal of Virology*, 40:745–751 (1981);

Wilson T. M. A., *Proc. Natl. Acad. Sci. USA*, 90:3134–3141 (1993)).

Thus, in a tenth aspect, the present invention is directed to a method of treating AIDS in a patient comprising administering to said patient a therapeutically effective amount of a transdominant negative integrase gene.

The transdominant negative integrase gene might advantageously be used in combination with any of a variety of other agents useful for gene therapy inhibition of HIV (Yu M., et al., *Gene Therapy*, 1:13–26 (1994) and Yamada O., et al., *Gene Therapy*, 1:38–45 (1994)).

Thus, in a eleventh aspect, the present invention is directed to a method of treating AIDS in a patient comprising administering to said patient a therapeutically effective amount of a transdominant negative integrase gene in combination with one or more agents selected from the group consisting of:

a) a transdominant negative gene such as, for example, a transdominant negative rev gene, a transdominant negative tat gene: a transdominant negative gag gene, a transdominant negative env gene, a transdominant negative vpx gene, and the like;

b) a soluble(s) CD4 gene such as, for example, a sCD4 gene, a sCD4-KDEL gene, and the like;

c) an intracellular antibody;

d) an interferon-inducible gene such as, for example, a RBP9-27 gene and the like;

e) a RNA decoy gene such as, for example, HIV-1 TAR, HIV-1 RRE, and the like;

f) an antisense RNA; and g) a ribozyme such as, for example, a hammerhead ribozyme, a hairpin ribozyme, and the like.

Preferably, the transdominant negative integrase gene might advantageously be used in combination with other transdominant negative HIV genes, for example, a rev gene (e.g., the rev M10 of Malim M. H., et al., *Cell*, 58:205–214 (1989)) and/or ribozymes that cleave HIV RNAs (Yamada O., et al., *Gene Therapy*, 1:38–45 (1994)). This would enable a greater degree of efficacy than would be achieved by any one gene.

Thus, in a twelfth aspect, the present invention is directed to a method of treating AIDS in a patient comprising administering to said patient a therapeutically effective amount of a transdominant negative integrase gene in combination with a transdominant negative rev gene.

In a most preferred embodiment of the twelfth aspect of the invention, the transdominant negative rev gene is rev M10.

In a thirteenth aspect, the present invention is directed to a method of treating AIDS in a patient comprising administering to said patient a therapeutically effective amount of a transdominant negative integrase gene in combination with a ribozyme that cleaves HIV RNA.

In a fourteenth aspect, the present invention is directed to a method of treating AIDS in a patient comprising administering to said patient a therapeutically effective amount of a transdominant negative integrase gene in combination with a transdominant negative rev gene and a ribozyme that cleaves HIV RNA.

In a fifteenth aspect, the present invention is directed to a pharmaceutical delivery method adapted for administration to a patient in an effective amount of an agent for treating a retroviral infection comprising a transdominant negative integrase gene and a suitable viral or nonviral delivery system.

In a preferred embodiment of the fifteenth aspect of the invention, the pharmaceutical delivery method is adapted for ex vivo or in vivo delivery.

In a most preferred embodiment of the fifteenth aspect of the invention, the pharmaceutical delivery method is directed to therapeutic or prophylactic administration.

In a sixteenth aspect, the present invention is directed to a method of treating AIDS in a patient comprising administering to said patient a therapeutically effective amount of a transdominant negative integrase gene in combination with an antiviral agent.

In a preferred embodiment of the sixteenth aspect of the invention, the antiviral agent is selected from the group consisting of a nucleoside or a nonnucleoside reverse transcriptase inhibitor, a HIV protease inhibitor, and a tat inhibitor.

In a most preferred embodiment of the sixteenth aspect of the invention, the reverse transcriptase inhibitor is selected from the group consisting of azidothymidine, dideoxyinosine, dideoxycytosine, and d4T.

In a seventeenth aspect, the present invention is directed to a method of treating AIDS in a patient comprising administering to said patient a therapeutically effective amount of a transdominant negative integrase gene in combination with interleukin-2.

BRIEF DESCRIPTION OF THE DRAWINGS

The invention is further described by the following non-limiting examples which refer to the accompanying FIG. 1, short particulars of which are given below.

FIG. 1 shows the amino acid (Seq. ID NO: 2) and nucleotide sequence (Seq. ID No: 1) of the synthetic gene which encodes the integrase protein reengineered with translation initiation sequences of mammalian cells.

DETAILED DESCRIPTION OF THE INVENTION

The term "transdominant" means that the effect of the gene is operational when the gene is expressed from some genetic element not necessarily linked to the virus.

The term "negative" means that the gene reduces replication of the retrovirus.

The term "transdominant negative" means a gene that can inhibit replication of a retrovirus without necessarily being genetically linked to the retrovirus.

The term "transdominant negative integrase gene" includes an intact retroviral integrase gene, fragments thereof, and both active and catalytically inactive mutants thereof.

The term "transfected gene" means a gene introduced into a cell by some exogenous means, such that a gene is added that the cell did not receive from the germ line of the animal from which it was derived.

The term "transient expression" means the expression of a transfected gene that is temporary, usually lasting only a few days.

The term "stable expression" means the expression of a transfected gene where the expression is sustained for weeks.

The term "HIV" includes HIV-1 and HIV-2.

The term "mammal" includes humans.

The present invention includes 293-CD4 cells. Human cells expressing the CD4 gene are generally infectable with HIV, since CD4 is the receptor used by HIV for cell entry. The literature teaches that candidate transdominant negative genes are tested by expressing the transfected gene in a stable cell line, and then testing that stable cell line for its ability to resist infection by HIV (see Yu M., et al., *Gene Therapy*, 1:13–26 (1994) and references cited therein). Making such a stable cell line expressing the candidate gene is laborious, taking more than 1 month of selection and screening cells for expression.

A faster method would be to use so-called "transient expression" of the candidate gene, where cells are tested within 24–48 hours after transfection. However, in most cell lines, transient expression is inefficient. Inefficiency refers to the percentage of cells in the population that take up and express the gene being introduced. In most cell lines, fewer than 10% and often around 1% of the cells in a population take up and express the transiently transfected gene. This would clearly be unacceptable for evaluating candidate transdominant negative genes, since if over 90% of a cell population remains untransfected and fully susceptible to HIV infection, a small percentage of resistant cells would not be experimentally detectable.

The present invention solves this problem by introducing the gene for CD4 in an expression vector into the transformed human kidney cell line 293 (available from American Type Culture Collection). This is exemplified in Example 1. The result is a cell line that can be transiently transfected at a frequency of greater than 50%, and by virtue of its CD4 expression, is infectable with HIV. This enables a test of candidate dominant negative genes by transfection and infection a day later.

This is both surprising and unexpected since it could not be predicted that such a cell line would be useful for testing candidate dominant negative genes. Thus, prior to the present disclosure, it was not known that 293-CD4 cells would be infectable with HIV or that the 293-CD4 cells would retain the highly efficient transient expression capability of the 293 cell parent. Moreover, prior to the present disclosure, it was not known that the kinetics of transient expression (e.g., expression of the transfected gene declines after about 2 days) would allow significant protection from an HIV challenge or that protection of 293-CD4 cells from HIV challenge by transient expression would be predictive for protection of a naturally susceptible cell population.

Therefore, the present invention affords a cell line and protocol that can be used to discover the transdominant negative effect of integrase genes; and that will be broadly useful in research on dominant negative mutants of HIV proteins, as well as other kinds of protective genes such as ribozymes.

Also, the present invention incudes a vector for production of HIV transdominant negative integrase in a mammalian cell incorporating a synthetic integrase gene, e.g., a DNA sequence which contains a substantial number of codons different from the natural codons such as, for example, 10 or more codons different from the natural codons or a fragment thereof that encodes at least 150 amino acids. Preferably, the DNA sequence is Seq ID No.: 1 or a DNA sequence containing 10 or less codons different from Seq ID No.: 1, or a fragment thereof that encodes at least 150 amino acids.

Additionally, the present invention includes transdominant negative retroviral integrase genes and methods to use these transdominant negative integrase genes to render cells resistant to retroviral infection. This would include making a population of cells in an HIV infected person resistant to HIV via delivery of such genes.

The transdominant negative retroviral integrase gene can be introduced into cells by any of the many methods known for introducing DNA into cells, either transiently or permanently. The methods for introducing DNA into cells include calcium phosphate co-precipitation, cationic liposomes, electroporation, receptor mediated endocytosis, particle-mediated gene transfer, or for some cell types, naked DNA can be used. The transdominant negative integrase genes can also be introduced by any of the well-known viral vectors, including retroviruses, adenovirus, adeno-associated virus, and herpes viruses. For some applications, e.g., making an animal resistant to a retrovirus, the transdominant negative integrase might be introduced into the germ line of an animal by the methods for making transgenic animals (including pronuclear microinjection, embryonic stem cells, and other technologies known in the art). Thus, the transdominant negative integrase gene of the present invention can be introduced into cells by conventional gene transfer technology known to those skilled in the art.

In addition, the transdominant negative integrase gene could be combined with any of the variety of other approaches for gene therapy inhibition of HIV (Yu M., et al., *Gene Therapy*, 1:13–26 (1994) and Yamada O., et al., *Gene Therapy*:1:38–45 (1994)).

Thus, the transdominant negative integrase gene may be combined with one or more agents selected from the group consisting of:

a) a transdominant negative gene such as, for example, a transdominant negative rev gene, a transdominant negative tat gene, a transdominant negative gag gene, a transdominant negative env gene, a transdominant negative vpx gene, and the like;

b) a soluble(s) CD4 gene such as, for example, a sCD4 gene, a sCD4-KDEL gene, and the like;

c) an intracellular antibody;

d) an interferon-inducible gene such as, for example, a RBP9-27 gene and the like;

e) a RNA decoy gene such as, for example, HIV-1 TAR, HIV-1 RRE, and the like;

f) an antisense RNA; and g) a ribozyme such as, for example, a hammerhead ribozyme, a hairpin ribozyme, and the like.

Preferably, a transdominant negative integrase gene of the present invention may be combined with a transdominant negative rev gene such as, for example, a transdominant negative rev M10 gene as described by Malim M. H., et al., *Cell*, 58:205–214 (1989) and/or a ribozyme that cleaves HIV RNAs. Ribozymes and methods for their preparation have been disclosed in U.S. Pat Nos. 4,987,071, 5,037,746, 5,116, 742, 5,093,246, and 5,180,818 which are hereby incorporated by reference.

Additionally, specific anti-HIV ribozymes have been disclosed in International Published Patent Applications WO 9401549-A1, WO 9324133-A1, WO 933569-A1, WO 9207065-A1, WO 9201806-A, WO 9110453-A, WO 9103162-A, WO 9013641-A; European Published Patent Application EP 360257-A, and U.S. Pat. No. 5,144,019 which are hereby incorporated by reference.

Optimal treatment of a patient receiving dominant negative integrase gene therapy will often involve coadministration with a chemical antiviral drug or interleukin-2. Currently approved drugs that can be combined with integrase gene therapy are azidothymidine, dideoxyinosine, dideoxycytosine, or d4T. The invention envisions combination with future antivirals in the classes of nucleoside and non-nucleoside reverse transcriptase inhibitors, HIV protease inhibitors, and tat inhibitors.

A suitable pharmaceutical delivery method for the dominant negative integrase genes is either by ex vivo or in vivo delivery. In the case of ex vivo delivery, $CD4^+T$ cells, monocytes, or hematopoietic progenitor cells, are removed by plasmapheresis from either the patient or a suitable donor. The dominant negative integrase gene is then introduced into these cells by transduction with a retroviral vector or by microprojectiles (Nabel G., et al., *Human Gene Therapy*, 5:79–92 (1994)). Alternatively, the genes could be introduced via adeno-associated virus (e.g., Zhou S. Z., et al., *J. Exp. Med.*, 179:1867–1875 (1994)) or liposomes. The transduced cells, either with or without selection for survival of transduced cells, are then administered to the patient to be treated. Usually a dose of $1 \times 10^7$ to $1 \times 10^{11}$ transduced T cells, or from 1 to $1 \times 10^6$ transduced hematopoietic progenitor cells are administered per course of treatment. The patient may be given repeat courses of treatment periodically as required to maintain a suitable level of transduced $CD4^+T$ cells, usually with 3 months to 3 years between treatments.

For in vivo delivery, a suitable viral or nonviral delivery system is used to administer the dominant negative integrase gene to the patient. This administration may be intravenous. The formulation could be, for example, using cationic liposomes (Philip R., et al., *J. Biol. Chem.*, 268:16087–16090 (1993)), where from 10 µg to 10 mg of a vector expressing the dominant negative integrase is delivered. For in vivo administration, it will usually be preferred to use a vector that will direct tissue-specific gene expression, e.g., the promoter of the human CD4 gene.

The following nonlimiting examples illustrate the inventor's preferred methods for preparing a transdominant negative integrase gene of the present invention.

EXAMPLE 1
Construction of 293-CD4 Cells 293 cells are a transformed human cell line (available from the American Type Culture Collection) that are particularly useful for efficient transient expression of transfected genes. The gene for human CD4 (the receptor for HIV) is introduced into these cells to make them susceptible to HIV infection.

Step A Preparation of RSV CD4 Expression Vector

A 3.0 kb fragment containing 1.8 kg of CD4 coding sequence is removed from the T4-pMV7 plasmid (Maddon P. J., et al., *Cell*, 47:333–348 (1986)) using EcoRI. The ends are made blunt by Klenow polymerase. The pRSV PAP plasmid (Lin, et al., *Biotechniques*, 3:344–348, 350–351 (1991)) is cut with HindIII and XbaI to remove the insert, and the ends made blunt with Klenow polymerase. The CD4 fragment is then ligated into the plasmid backbone.

Step B Preparation of 293-CD4 Cells

A calcium phosphate transfection is performed to introduce the RSV-CD4 vector into 293 cells, using the method described in Sambrook J., et al., *Molecular Cloning. A Laboratory Manual*, Cold Spring Harbor Laboratory Press, 1989, 16.30–16.40. The cells are transfected at 20% confluence, washed with Dulbecco's Modified Eagle's Medium (DMEM) plus 10% fetal calf serum 24 hours posttransfection, and selected in G418 at 0.5 mg/mL 48 hours posttransfection. Following G418 selection, individual clones are isolated and screened by fluorescence activated cell sourcing (FACS) for CD4 using a monoclonal antibody to CD4.

Figure 1:
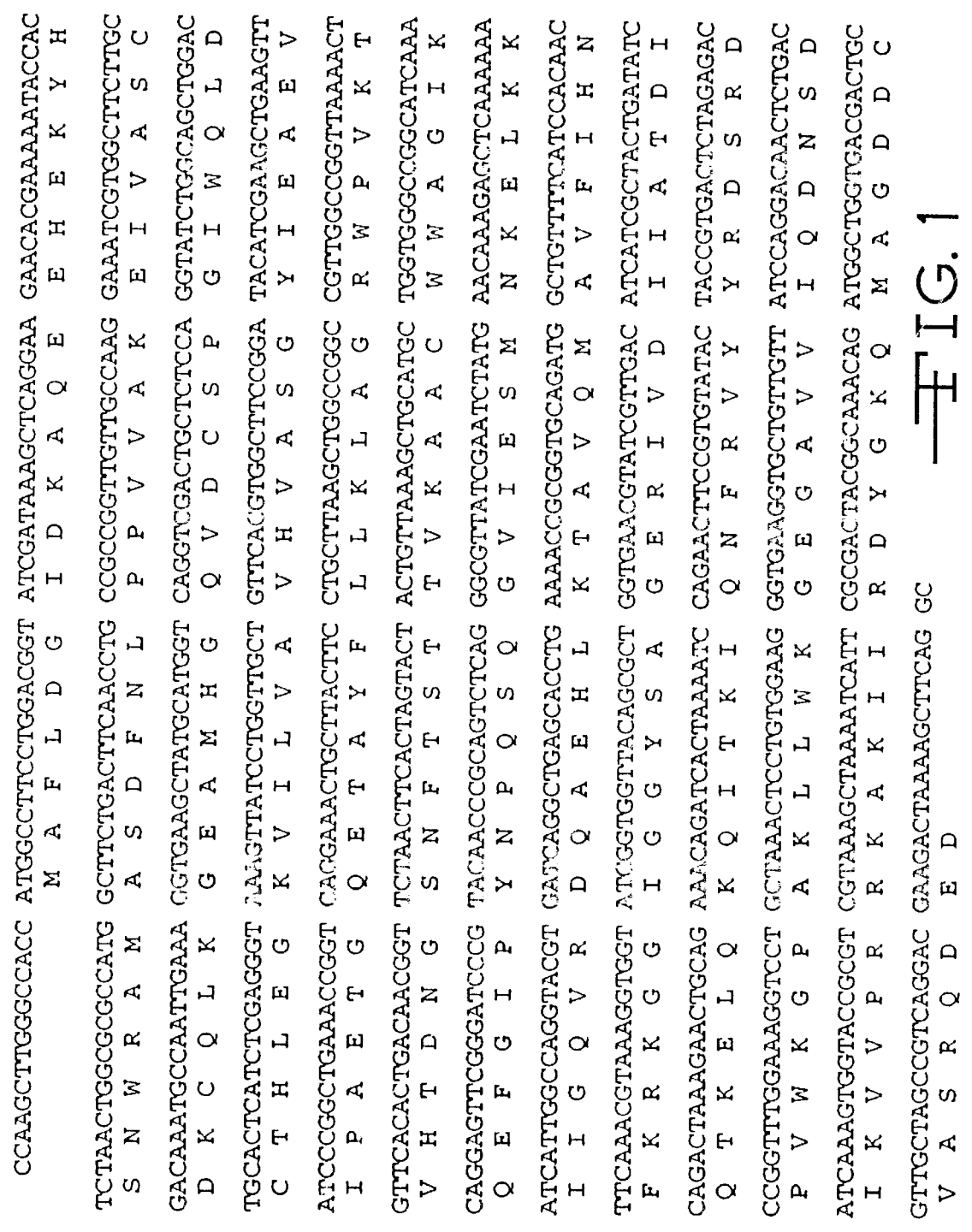

EXAMPLE 2
Construction of a Vector Expressing HIV Integrase in Mammalian Cells Using a Synthetic Gene The synthetic genes coding for wild-type ("NdeI") and an inactive mutant ("D116N") integrase (IN) had previously been cloned into the *E. coli* expression vector pKK223 (Holler T. P., et al., *Gene*, 136:323–328 (1993)). Constructs for the NdeI and D116N gene are done in parallel; all manipulations described are done for both genes. The first unique restriction site in the synthetic gene is a ClaI site at nucleotide 17 (relative to the ATG). The plasmid pKK223/NY5IN-NdeI (or D 116N) is digested with ClaI and dephosphorylated using bacterial alkaline phosphatase (BRL). Synthetic oligonucleotides ALM 1 (5'-CCAAGCTGG GCCACCATG GCC TTC CTG GAC GGT AT-3') (Seq ID No: 3) and its complement ALM 2 (5'- CGAT ACC GTC CAG GAA GGC CAT GGT GGC CCA AGC TTGG-3') (Seq ID No: 4) containing a HindIII site at the 5' end, a ClaI site at the 3' end, and a Kozak consensus (underlined) (Kozak M., *Journal of Biological Chemistry*, 266:19867–19870 (1991)) for translation initiation are synthesized on an ABI oligonucleotide synthesizer. Following gel purification, the oligos are annealed and the ends of the fragment phosphorylated using T4 polynucleotide kinase (NEB) and ATP. The oligonucleotide pair ALM 1/2 was ligated to the linearized pKK223/NY5IN-NdeI (D116N) and the product of the ligation reaction digested with HindIII, to expose the HindIII site on the 5' end (from the oligos), and to remove the entire IN coding sequence from the bacterial expression vector. The IN gene, optimized for mammalian translation, is isolated from the agarose gel. The sequence of the synthetic gene so modified for translation in mammalian cells (Seq ID No.: 1) is shown in FIG. 1. The mammalian expresion vector pRcRSV is purchased from Invitrogen. Plasmid pRcRSV is digested with HindIII and the ends dephosphorylated. Linearized plasmid is isolated from an agarose gel. The IN gene is ligated into the HindIII site of pRcRSV to produce the plasmid pRSV/IN-NdeI (D116N). Correct orientation of the insert is determined by restriction endonuclease digestion, and the sequence at the 5' end of the gene (through the ClaI site) confirmed by DNA sequencing.

EXAMPLE 3
Demonstration of Transdominant Negative Activity of Integrase Expression A vector expressing the synthetic gene of integrase is demonstrated to have dominant negative activity against HIV infection by the following experiment. The integrase gene is transiently expressed in 293-CD4 cells, which are subsequently infected by HIV. The cells expressing HIV integrase support HIV replication substantially less than cells with no integrase.

The 293-CD4 cells are split into 6-well plates at a cell density of $2-4 \times 10^5$ per well. Cells are allowed to attach and grow for 6 hours prior to transfections with the expression vector DNA. Following the protocol of Example 4 for 293 cell 10 transfections, the cells are incubated with calcium phosphate precipitates for 24 hours. The medium on the cells is then changed immediately prior to infection with HIV-1.

$4-8 \times 10^4$ Infectious HIV-IIIB particles are added i15 per well. Infection is allowed to proceed for approximately 12 hours, and then the medium is changed.

At various times after infection, samples of medium are removed for reverse transcriptase assay following the protocol of Example 5.

The following data is an example of the counts per minute obtained in the reverse transcriptase assay from samples from such an assay:

| Day PostInfection | Vector | pRSV/IN-NdeI |
| --- | --- | --- |
| Day 2 | 1054 | 1181 |
| Day 3 | 1280 | 962 |
| Day 4 | 2682 | 1802 |
| Day 5 | 5607 | 2792 |

This, and other experiments, establishes that expression of integrase can substantially slow infection of HIV.

It should be noted that absolute blockage of viral replication cannot be expected in a transient expression system, since not all of the cells are expressing integrase.

EXAMPLE 4
Protocol for Transfection of 293 Cells

The transfection protocol has been modified for use specifically on 293 and 293/CD4+cell lines. The same protocol is used for the expression and transdominant experiments to introduce expression vectors. Transfection efficiencies as high as 85–90% are routinely observed.

| Solutions | | |
|---|---|---|
| HBSS: | Dextrose (6 mM) | 1.19 g |
| | NaCl (137 mM) | 8.01 g |
| | KCl (5 mM) | 0.37 g |
| | $Na_2HPO_4$ (0.7 mM) | 0.10 g |
| | Hepes Na + (21 mM) | 5.47 g |
| | dissolve in 1000 mL $ddH_2O$ pH solution to 7.05 with NaOH | |
| 2M $CaCl_2$: | 29.4 g/100 mL $ddH_2O$ | |

Protocol
1. The 293 cell line is split out into appropriate tissue culture dishes.

Transdominant assay: 6-well plates
Expression study: 10 $cm^2$ dishes
The cells are allowed to adhere and spread for 6 hours prior to transfection.
2. Place 5 μg of vector DNA into 250 μL of HBSS (sufficient for one 6-well or one 10 $cm^2$ dish).

Add 31 μ of 2M $CaCl_2$ and vortex gently for 1 to 2 minutes to thoroughly mix.
3. Incubate at room temperature for 45 minutes; precipitate more than likely will not be visible.
4. Add the $CaPO_4$/DNA precipitate directly to a minimal amount of tissue culture media covering the cells.

6-well plate: 2 mL/well
10 $cm^2$ dish: 5 mL/dish
5. Incubate cells in the presence of precipitate overnight at 37° C. Do not glycerol shock or you will lose the majority of cells.
6. The next morning, aspirate off the old media and replace with new media. Then incubate for the necessary length of time for the experiment.

EXAMPLE 5

Protocol for Reverse Transcriptase Assay

The reverse transcriptase (RT) assay measures the expression of viral proteins in the cultures.

| RT reaction cocktail = 1.25 × RT reaction shock | | | |
|---|---|---|---|
| 50 mM | Tris pH 8.3 | 10 mL 1M |
| 75 mM | KCl | 15 mL 1M |
| 10 mM | $MgCl_2$ | 2 mL 1M |
| 10 mM | DTT | 2 mL 1M |
| 1 mM | EGTA | 76 mg |
| 0.5% | NP-40 | 1 mL 10% |
| 100 μg/mL | poly rA | 2 mL 10 mg/mL |
| 25 μg/mL | oligo dT 100 $A_{260}$ units (1 bottle) | 128 mL $dH_2O$ |

8 μCi/mL $^{32}$P-dATP (400 Ci/mmol) is added immediately before assay.
Protocol
1. Place two GeNunc polypropylene modules (120 μL, Cat #2-32549) in a GeNunc frame (Cat #2-32042) for each assay plate.
2. Transfer 5 μL of culture media from each well of the assay plate to the corresponding well of the GeNunc module. Using a 12-channel pipettor, transfer row H, change tips, and complete the rest of the plate starting at row A and moving to row G. By moving from the lowest to highest RT activity, the rest of the plate can be transferred without changing tips.
3. Prepare 2.5 mL RT reaction cocktail for each plate by adding 2.5 μL $^{32}$P-dATP (400 Ci/mmol, 10 μCi/μL) to 2.5 mL 1.25×RT reaction stock.
4. Dispense 2.5 mL RT reaction cocktail into the trough of an 8-channel reagent reservoir for each assay plate. Use a P1,000 pipetman so that the radioactive tip can be discarded in the Ziplock waste bag.
5. Add 20 μL RT reaction cocktail to each well of the GeNunc module. Using a 12-channel pipettor, transfer row H, change tips, and finish the rest of the plate stating at row A and moving to row G. By moving from the lowest to highest RT activity, the rest of the plate can be filled from one trough of the reagent reservoir without changing tips.
6. Cover the wells with GeNunc adhesive tapes (Cat #232700).
7. Incubate 2 hours, 37° C.
8. Mark a 96-well array on a sheet of Whatman DE81 anion exchange filter paper using the rubber stamp.
9. Spot 4 μL of the RT reaction from each well of the GeNunc module onto the corresponding mark of the DE81 filter. Using a 12-channel pipettor, transfer row H, change tips, and finish the rest of the module starting at row A and moving to row G. By moving from the lowest to highest RT activity, the rest of the module can be spotted without changing tips.
10. Wash the filter five times, 3 minutes each, in 2×SSC (300 mM NaCl, 30 mM NaCitrate, pH 7).
11. Rinse the filter twice in 95% ethanol.
12. Air dry the filter.
13. Quantitate the RT activity by counting the incorporated $^{32}$p for each well using the Betagen Betascope 603 with the slot/dot blot analysis program as described in the applications manual.

Data is collected for 30 minutes in the $^{32}$P mode and reported as total counts per well.

EXAMPLE 6

Construction of a CEM Cell Line Expressing HIV-1 Integrase

CEM cells are a line of $CD4^+$human lymphoblastoid cells (obtainable from American Type Culture Collection). CEM cells were maintained in RPMI 1640 medium supplemented with 10% fetal calf serum, 50 U/mL penicillin, 50 U/mL streptomycin. All tissue culture reagents were obtained from Gibco BRL, Gaithersburg, MD. CEM cells were transfected by electroporation according to the method of Aldovini and Feinberg (pp. 147–159 in: Techniques in HIV Research, Stockton Press, New York, NY, 1990). Twenty micrograms each of plasmid DNA (either pRc/RSV, pRSV/IN-Nde, or pRSV/IN-D116N) were added to a 0.4 mL suspension of 5 million CEM cells in serum free RPMI 1640 medium. The DNA-cell suspensions were incubated on ice for 10 minutes in a Gene Pulsar cuvette and then subjected to a single pulse of 960 μF at 300 volts using a Bio-Rad Gene Pulsar Electroporator (Bio-Rad, Richmond, Calif. Following electroporation, the cells were incubated on ice for 10 minutes and then diluted in 10 mL RPMI 1640 medium with 10% fetal calf serum. The cells were incubated in 75 $cm^2$ tissue culture flasks at 37° C. in a 5% $CO_2$ incubator for 48 hours. The cells from each flask were centrifuged to pellet the cells and the supernatants removed. The cell pellets were diluted in RPMI 1640 medium supplemented with 10% fetal calf serum and 750 μg/mL G418 (Geneticin, Gibco BRL) at a density of 200,000 cells per mL. The diluted cells were transferred to 96 well plates, 100 μL/well, and incubated at 37° C. for 7 days. The G418 selection was then increased to 1 mg/mL. Colonies appeared in 2–3 weeks. These colonies were transferred to 6 well plates and were diluted in 3 mL RPMI 1640 medium plus 1 mg/mL G418.

After the cells had reached a density of 1,000,000 cells per mL, they were screened by western blot techniques for expression of HIV-1 integrase, using a polyclonal rabbit antiserum prepared against integrase produced in *E. coli* (Holler T. P., et al., *Gene*, 136:323–328 (1993)). The procedure used for this western blot is described. One million cells were suspended in Laemmli buffer, and loaded onto a 12% polyacrylamide gel. The separated protein bands were transferred to nitrocellulose paper by electroblotting. The blots were blocked with 10% nonfat dry milk in phosphate buffered saline (PBS) plus 0.3% tween 80 for 1 hour. The blocked blots were then incubated for 2 hours with a 1/1000 dilution of the rabbit antiserum. The blots were then washed 3 times in PBS/tween, then incubated for 1 hour with a 1/2000 dilution of goat antirabbit IgG conjugated with horseradish peroxidase. After 4 washes in PBS-tween, the integrase expression was detected with an enhanced chemiluminescence (ECL) kit (Amersham, Arlington Heights, IL). Of 50 wells which grew under G418 expression, two each expressing wild type integrase or D116N were obtained.

EXAMPLE 7

Demonstration of Protection Against HIV Infection in CEM Cells Expressing a Dominant Negative Integrase Gene CEM cell lines prepared in Example 6 were grown in the presence of 1 mg/mL G418, and density adjusted to $4 \times 10^6$ cells/mL. Fifty microliters of suspended cells was combined with 40 μL HIV stock virus ($2 \times 10^3$ pfu/mL) and 10 μL medium. Cells and virus were coincubated at 37° C. for 2 hours, then washed once in 1 mL medium. Each washed pellet was resuspended in 3 mL medium, then 1 mL aliquots were plated in triplicate wells of a 24 well plate. Fifty microliter samples were taken from each well of infected cells on days 1–5 and 7 postinfection. Cell cultures were split 1:3 on days 3 and 5 after sampling, by adding 2 mL medium, mixing the culture, then removing 2 mL of medium and infected cells. The data is not corrected for these splits.

The samples were assayed using the reverse transcriptase assay described in Example 5. The counts per minute from the triplicate samples at each time point were averaged.

| Day | Control Vector | Nde | D116N |
| --- | --- | --- | --- |
| 1 | 598 | 2325 | 2035 |
| 2 | 1177 | 1701 | 1905 |
| 3 | 1947 | 1806 | 2260 |
| 4 | 6776 | 3102 | 3396 |
| 5 | 6815 | 2768 | 2935 |
| 7 | 22922 | 9820 | 7542 |

This experiment shows that expression of either the wild type integrase (Nde) or the D116N mutant retards the growth of HIV-1 in a human lymphoblastoid cell line, as predicted by the results in the 293-CD4 cells.

It should be noted that since these cells were not cloned before testing, even though all were G418 resistant, not all of them were expressing integrase. Therefore, the level of protection observed is a minimal level to be expected in a population expressing the dominant negative integrase genes.

What is claimed is:

1. An isolated nucleic acid sequence comprising a nucleic acid sequence encoding the polypeptide of SEQ ID NO:2.

2. A vector comprising an isolated nucleic acid sequence encoding the polypeptide of SEQ ID NO:2.

3. The vector of claim 2, wherein the nucleic acid sequence comprises SEQ ID NO:1.

4. The vector of claim 2, wherein the vector is selected from the group consisting of pRSV/IN-NdeI and pRSV/IN-D116N.

5. The vector of claim 2, wherein the vector is pRSV/IN-NdeI.

6. A method of making a vector encoding the polypeptide of SEQ ID NO:2 comprising inserting an isolated nucleic acid sequence encoding the polypeptide of SEQ ID NO:2 into a vector.

7. The method of making a vector of claim 6, wherein the nucleic acid sequence comprises SEQ ID NO:1.

8. The method of making a vector of claim 6, wherein the vector is selected from the group consisting of pRSV/IN-NdeI and pRSV/IN-D116N.

9. The method of making a vector of claim 6, wherein the vector is pRSV/IN-NdeI.

10. A method of transfecting a cell in vitro comprising transfecting an isolated cell with a vector comprising a nucleic acid sequence encoding the polypeptide of SEQ ID NO:2 such that the cell functionally expresses the polypeptide.

11. The method of transfecting a cell in vitro of claim 10, wherein the nucleic acid sequence comprises SEQ ID NO:1.

12. The method of transfecting a cell in vitro of claim 10, wherein the vector comprising a nucleic acid sequence encoding SEQ ID NO:2 is selected from the group consisting of pRSV/IN-NdeI and pRSV/IN-D116N.

13. The method of transfecting a cell in vitro of claim 12, wherein the vector comprising a nucleic acid sequence encoding SEQ ID NO:2 is pRSV/IN-NdeI.

14. The method of transfecting a cell in vitro of claim 10, wherein the cell is a mammalian cell or an avian cell.

15. The method of transfecting a cell in vitro of claim 14, wherein the mammalian cell is 293-CD4.

16. The method of transfecting a cell in vitro of claim 14, wherein the mammalian cell is a human cell.

17. The method of transfecting a cell in vitro of claim 16, wherein the human cell is a CD4+ T lymphocyte or a monocyte.

18. The method of transfecting a cell in vitro of claim 16, wherein the human cell is hematopoietic progenitor cell.

19. The method of transfecting a cell in vitro of claim 10, wherein the cell is transfected using calcium phosphate co-precipitation, a complex of cationic liposomes, electroporation, naked DNA, or a viral vector.

20. The method of transfecting a cell in vitro of claim 19, wherein the viral vector is selected from the group consisting of a retroviral vector; an adenoviral vector; an adeno-associated viral vector; and a herpes viral vector.

21. A method of making the retroviral integrase of SEQ ID NO:2 comprising:

a) making a vector encoding the polypeptide of SEQ ID NO:2 comprising inserting an isolated nucleic acid sequence encoding the polypeptide of SEQ ID NO:2 into a vector;

b) transfecting an isolated cell with a vector comprising a nucleic acid sequence encoding the polypeptide of SEQ ID NO:2 such that the cell functionally expresses the polypeptide; and c) isolating the polypeptide of SEQ ID NO:2.

22. The method of making the retroviral integrase of SEQ ID NO:2 of claim 21, wherein the nucleic acid sequence comprises SEQ ID NO:1.

* * * * *